United States Patent [19]
Garner et al.

[11] Patent Number: 5,959,135
[45] Date of Patent: Sep. 28, 1999

[54] HYDROCYANATION PROCESSES AND MULTIDENTATE PHOSPHITE LIGAND AND NICKEL CATALYST COMPOSITIONS THEREOF

[75] Inventors: James Michael Garner, Wilmington, Del.; Wilson Tam, Boothwyn, Pa.

[73] Assignee: E. I. du Pont de Nemours and Company, Wilmington, Del.

[21] Appl. No.: 09/111,907

[22] Filed: Jul. 8, 1998

Related U.S. Application Data

[60] Provisional application No. 60/054,075, Jul. 29, 1997.

[51] Int. Cl.$^6$ .................................................. C07C 253/00
[52] U.S. Cl. ............................................................... 558/338
[58] Field of Search ............................................... 558/338

[56] References Cited

U.S. PATENT DOCUMENTS

| | | | |
|---|---|---|---|
| 3,496,215 | 2/1970 | Drinkard et al. | 260/465.8 |
| 3,496,217 | 2/1970 | Drinkard, Jr. et al. | 260/465.8 |
| 3,496,218 | 2/1970 | Drinkard, Jr. et al. | 260/465.8 |
| 3,631,191 | 12/1971 | Kane et al. | 260/439 R |
| 3,655,723 | 4/1972 | Drinkard, Jr. | 260/465.3 |
| 3,766,237 | 10/1973 | Chia et al. | 260/465.3 |
| 4,774,353 | 9/1988 | Hall et al. | 558/335 |
| 4,874,884 | 10/1989 | McKinney et al. | 558/338 |
| 5,512,696 | 4/1996 | Kreutzer et al. | 558/338 |

FOREIGN PATENT DOCUMENTS

| | | | |
|---|---|---|---|
| WO 93/03839 | 3/1993 | WIPO | B01J 31/24 |
| WO 96/11182 | 4/1996 | WIPO | C07C 253/10 |
| WO 96/22968 | 8/1996 | WIPO | C07C 253/10 |

OTHER PUBLICATIONS

Tolman et al., *Advances in Catalysis*, 33, 1, 1985.
M.J. Baker et al., *J. Chem. Soc. Chem. Commun.*, 1292, 1991.
Baker et al., *J. Chem. Soc. Chem. Commun.*, 803, 1991.
Cuny et al., *J. Am. Chem. Soc.*, 115, 2066, 1993.

*Primary Examiner*—Robert W. Rawsuer
*Assistant Examiner*—Joseph Murray

[57] ABSTRACT

A process for hydrocyanation of an aliphatic monoethylenically unsaturated compound, in which the ethylenic double bond is not conjugated to any other unsaturated group in the molecule, which process uses a catalyst composition comprising a zero-valent nickel and a multidentate phosphite ligand in the presence of a Lewis acid promoter.

8 Claims, No Drawings

HYDROCYANATION PROCESSES AND MULTIDENTATE PHOSPHITE LIGAND AND NICKEL CATALYST COMPOSITIONS THEREOF

This application claims the priority benefit of U.S. Provisional Application Ser. No. 60/054,075, filed Jul. 29, 1997.

FIELD OF THE INVENTION

The invention generally relates to a process and catalyst precursor composition for the hydrocyanation of monoethylenically unsaturated compounds herein zero-valent nickel and a multidentate phosphite ligand are used in the presence of a Lewis acid promoter. In particular, the ligands contain naphthol groups.

BACKGROUND OF THE INVENTION

Hydrocyanation catalyst systems, particularly pertaining to the hydrocyanation of ethylenically unsaturated compounds, are known in the art. For example, systems useful for the hydrocyanation of butadiene to form pentenenitrile (PN) and in the subsequent hydrocyanation of pentenenitrile to form adiponitrile (ADN), are known in the commercially important nylon synthesis field.

The hydrocyanation of ethylenically unsaturated compounds using transition metal complexes with monodentate phosphite ligands is documented in the prior art. See, for example, U.S. Pat. Nos. 3,496,215; 3,631,191; 3,655,723; and 3,766,237, and Tolman et al., *Advances in Catalysis*, 1985, 33, 1. The hydrocyanation of activated ethylenically unsaturated compounds, such as with conjugated ethylenically unsaturated compounds (e.g., butadiene and styrene), and strained ethylenically unsaturated compounds (e.g., norbornene) proceeds without the use of a Lewis acid promoter, while hydrocyanation of unactivated ethylenically unsaturated compounds, such as 1-octene and 3-pentenenitrile, requires the use of a Lewis acid promoter.

Teachings regarding the use of a promoter in the hydrocyanation reaction appear, for example, in U.S. Pat. No. 3,496,217. This patent discloses an improvement in hydrocyanation using a promoter selected from a large number of metal cation compounds with a variety of anions as catalyst promoters. U.S. Pat. No. 3,496,218 discloses a nickel hydrocyanation catalyst promoted with various boron-containing compounds, including triphenylboron and alkali metal borohydrides. U.S. Pat. No. 4,774,353 discloses a process for the preparation of dinitriles, including ADN, from unsaturated nitriles, including PN, in the presence of a zero-valent nickel catalyst and a triorganotin catalyst promoter. Moreover, U.S. Pat. No. 4,874,884 discloses a process for producing ADN by the zero-valent nickel-catalyzed hydrocyanation of pentenenitriles in the presence of a synergistic combination of promoters selected in accordance with the reaction kinetics of the ADN synthesis.

Phosphite ligands have been shown to be useful ligands in the hydrocyanation of activated ethylenically unsaturated compounds. See, for example, Baker, M. J., and Pringle, P. G., *J Chem. Soc., Chem. Commun.*, 1991, 1292; Baker et al., *J Chem. Soc., Chem. Commun.*, 1991, 803; Union Carbide, WO 93,03839. Also, phosphite ligands have been disclosed with rhodium in the hydroformylation of functionalized ethylenically unsaturated compounds: see, Cuny et al., *J Am. Chem. Soc.*, 1993, 115, 2066.

U.S. Pat. No. 5,512,696, which issued Apr. 30, 1996, discloses processes and catalyst compositions for the hydrocyanation of monoethyleneically unsaturated compounds using zero-valent nickel and certain multidentate phosphite ligands, and Lewis acid promoters, which are similar to those encompassed by the present invention, except for the choice of naphthol groups instead of phenol groups on the phosphite ligands.

Like U.S. Pat. No. 5,512,696, the present invention provides processes and catalyst precursor compositions which are more rapid, selective, efficient and stable than prior processes and catalyst complexes employed in the hydrocyanation of monoethylenically unsaturated compounds. Other objects and advantages of the present invention will become apparent to those skilled in the art upon reference to the detailed description of the invention which hereinafter follows.

SUMMARY OF THE INVENTION

The present invention provides for a hydrocyanation process, comprising reacting an acyclic, aliphatic, monoethylenically unsaturated compound in which the ethylenic double bond is not conjugated to any other olefinic group in the molecule with a source of HCN in the presence of a catalyst precursor composition comprising a Lewis acid, a zero-valent nickel, and at least one multidentate phosphite ligand selected from the group represented by the following Formulas I, II, III, IV, V, VI, VII and VIII, in which all like reference characters have the same meaning, except as further explicitly limited.

Formula I
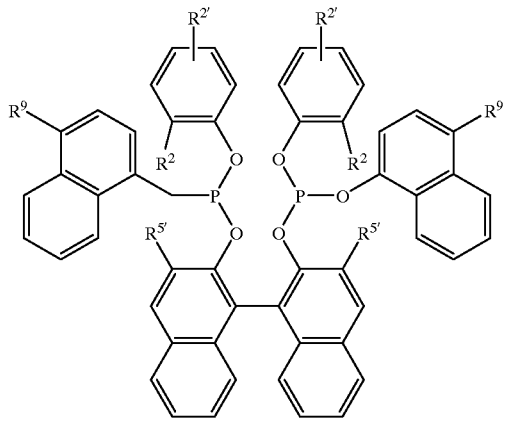
Formula II
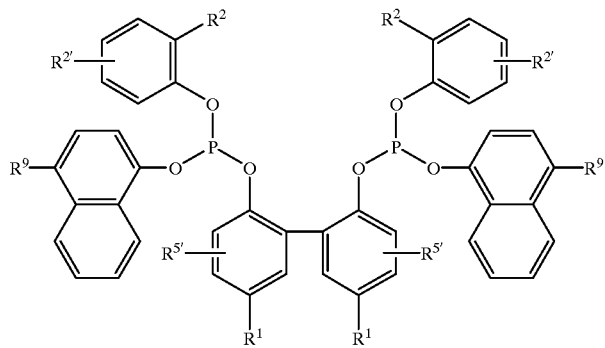
Formula III
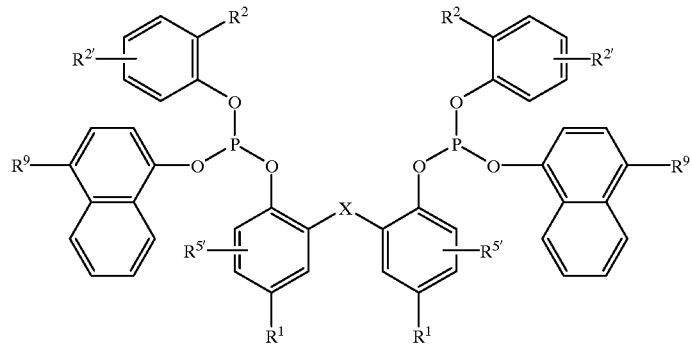
Formula IV
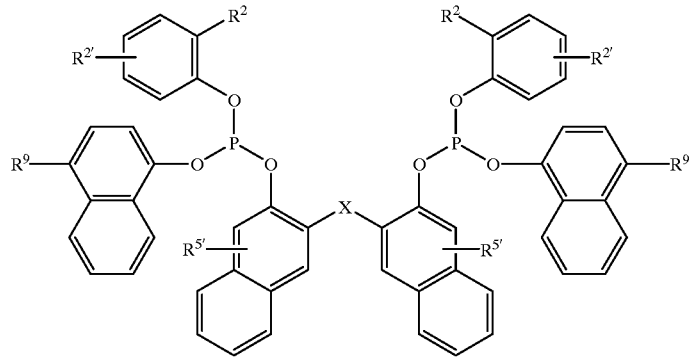

Formula V
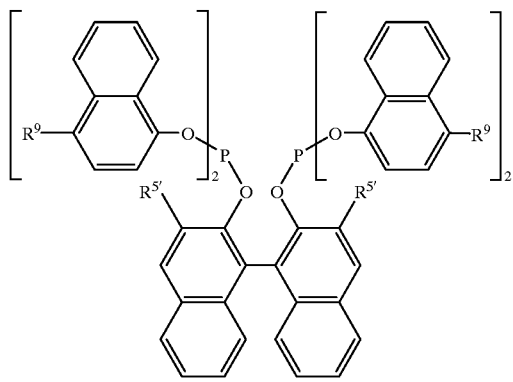
Formula VI
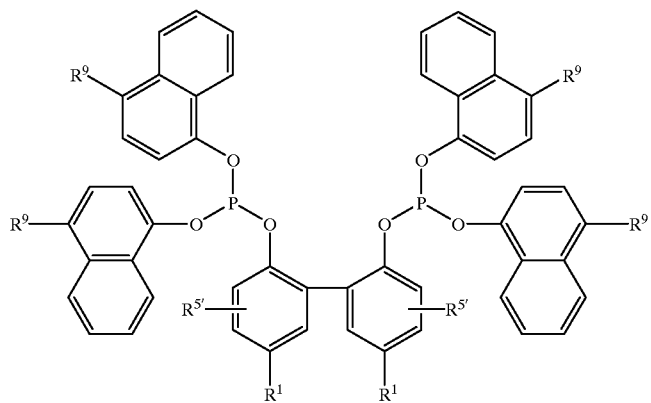
Formula VII
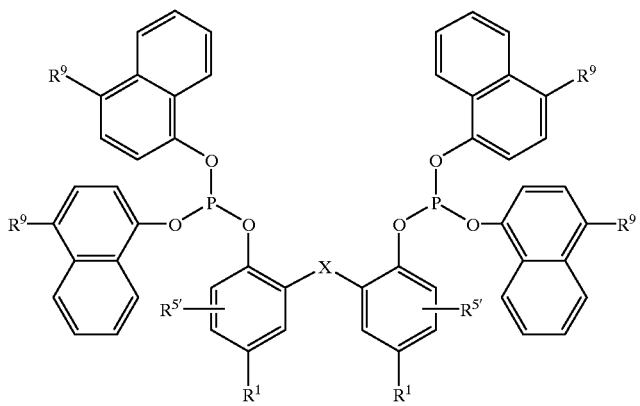

-continued

Formula VIII

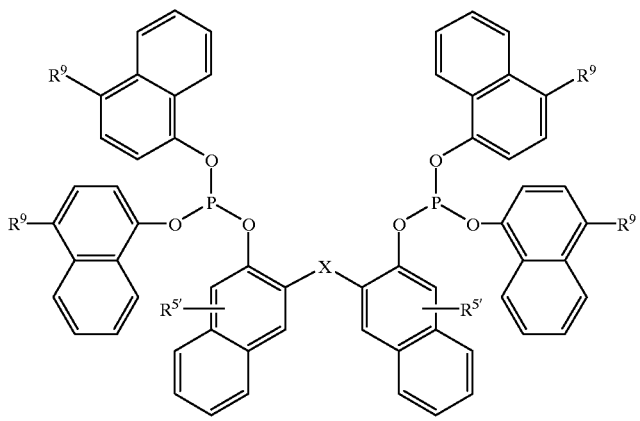

wherein each $R^1$ is independently a H, halogen, primary, secondary, or tertiary hydrocarbyl of 1 to 12 carbon atoms, $OR^3$ wherein $R^3$ is a $C_1$ to $C_{12}$ alkyl, or $CO_2R^{3'}$ wherein $R^{3'}$ is a $C_1$ to $C_{12}$ alkyl, or aryl;

each $R^2$ and $R^{2'}$ are independently a H, halogen, primary, secondary or tertiary hydrocarbyl of 1 to 12 carbon atoms, $OR^3$ wherein $R^3$ is a $C_1$ to $C_{12}$ alkyl, or $CO_2R^{3'}$ wherein $R^{3'}$ is a $C_1$ to $C_{12}$ alkyl, or aryl; when $R^{2'}$ is not hydrogen, $R^{2'}$ cannot be ortho to the oxygen;

each $R^{5'}$ is independently a H, halogen, primary, secondary or tertiary hydrocarbyl of 1 to 12 carbon atoms, $OR^3$ wherein $R^3$ wherein $R^3$ is a $C_1$ to $C_{12}$ alkyl, or $CO_2R^{3'}$ wherein $R^{3'}$ is a $C_1$ to $C_{12}$ alkyl, or aryl;

each $R^9$ is independently H, halogen, primary, secondary or tertiary hydrocarbyl or 1 to 12 carbon atoms, $OR^3$ wherein $R^3$ is a $C_1$ to $C_{12}$ alkyl, or $CO_2R^{3'}$ wherein $R^{3'}$ is a $C_1$ to $C_{12}$ alkyl, or aryl; and each X is independently O or $CH(R^{4'})$, wherein $R^{4'}$ is H, aryl, or a $C_1$ to $C_{12}$ alkyl.

The terms "secondary" and "tertiary" herein refer to the carbon atom bonded to an aromatic ring.

In the above catalyst precursor compositions, the Lewis acid is considered to be a promoter.

The term "hydrocarbyl" is well known in the art and designates a hydrocarbon molecule from which one hydrogen atom has been removed. Such molecules can contain single, double or triple bonds.

DETAILED DESCRIPTION OF THE PREFERRED EMBODIMENTS

Representative ethylenically unsaturated compounds which are useful in the process of this invention are shown in Formulas IX or XI, and the corresponding terminal nitrile compounds produced are illustrated by Formulas X or XII, respectively, wherein like reference characters have same meaning.

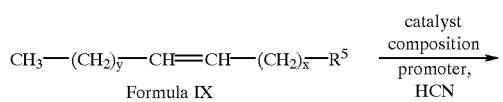

Formula IX

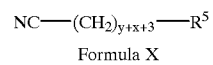

Formula X

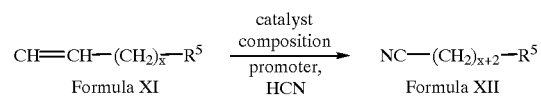

Formula XI    HCN    Formula XII wherein $R^5$ is H, CN, $CO_2R^{3'}$, or perfluoroalkyl;

y is an integer of 0 to 12;

x is an integer of 0 to 12 when $R^5$ is H, $CO_2R^{3'}$ or perfluoroalkyl;

x is an integer of 1 to 12 when $R^5$ is CN; and $R^{3'}$ is $C_1$ to $C_{12}$ alkyl, or aryl.

The catalyst composition of the invention may be considered a "precursor" composition in that the zero-valent nickel at some point becomes complexed to the multidentate phosphite ligand, and, further in all likelihood, additional reactions occur during hydrocyanation, such as, for example, complexing of the initial catalyst composition to an ethylenically unsaturated compound.

These ligands can be prepared by a variety of methods known in the art, for example, see descriptions in European Patent Application 92109599.8 of Mitsubishi Kasei Corporation and the corresponding U.S. Pat. No. 5,235,113 to Sato et al. The reaction of 4-methoxy-1-naphthol with phosphorus trichloride gives the phosphorochloridite. The reaction of this phosphorochloridite with 2,2'-dihydroxy-5,5'-dimethoxy-1,1'-biphenylene in the presence of triethylamine base gives a ligand of Formula VI.

The phosphorochloridite may be prepared by a variety of methods known in the art, for example, see descriptions in Polymer, 1992, 33, 161; *Inorganic Synthesis,* 1966, 8, 68;.U.S. 5,210,260; *Z. Anorg. Allg. Chem.,* 1986, 535, 221. With bulky ortho-substituted phenols (e.g., 2-t-butylphenol), phosphorochloridites can be prepared in situ from $PCl_3$ and the phenol. With less bulky groups, purification by high vacuum distillation is typically necessary. High vacuum distillation is difficult for large scale operations. An improved process for preparing the phosphochlorodite comprises treatment of N,N-dialkyl diarylphosphoramidite with HCl. $ClP(OMe)_2$ has been prepared in this manner, see *Z Naturforsch,* 1972, 27B, 1429. Phosphorochloridites derived from substituted phenols have been prepared using this procedure as described in copending commonly assigned application Serial No. 08/563,718, filed Nov. 28, 1995. It has also been found that phosphorochloridite of 1-naphthols can be prepared in situ from $PCl_3$ and 1-naphthols in the presence of a base like triethylamine.

The zero-valent nickel compounds can be prepared or generated according to techniques well known in the art, as described, for example, in U.S. Pat. Nos. 3,496,217; 3,631,191; 3,846,461; 3,847,959; and 3,903,120, which are incorporated herein by reference. Zero-valent nickel compounds that contain ligands which can be displaced by the organophosphorus ligand are a preferred source of zero-valent nickel. Two such preferred zero-valent nickel compounds are $Ni(COD)_2$ (COD is 1,5-cyclooctadiene) and $Ni\{P(O\text{-}o\text{-}C_6H_4CH_3)_3\}_2(C_2H_4)$, both of which are known in the art. Alternatively, divalent nickel compounds may be combined with a reducing agent, to serve as a source of zero-valent nickel in the reaction. Suitable divalent nickel compounds include compounds of the formula $NiY_2$ where Y is halide, carboxylate, or acetylacetonate. Suitable reducing agents include metal borohydrides, metal aluminum hydrides, metal alkyls, Zn, Fe, Al, Na, or $H_2$. Elemental nickel, preferably nickel powder, when combined with a halogenated cataylst, as described in U.S. Pat. No. 3,903,120, is also a suitable source of zero-valent nickel.

The nonconjugated acyclic, aliphatic, monoethylenically unsaturated starting materials useful in this invention include unsaturated organic compounds containing from 2 to approximately 30 carbon atoms. 3-Pentenenitrile and 4-pentenenitrile are especially preferred. As a practical matter, when the nonconjugated acyclic aliphatic monoethylenically unsaturated compounds are used in accordance with this invention, up to about 10% by weight of the mono-ethylenically unsaturated compound may be present in the form of a conjugated isomer, which itself may undergo hydrocyanation. For example, when 3-pentenenitrile is used, as much as 10% by weight thereof may be 2-pentenenitrile. (As used herein, the term "pentenenitrile" is intended to be identical with "cyanobutene"). Suitable unsaturated compounds include unsubstituted hydrocarbons as well as hydrocarbons substituted with groups which do not attack the catalyst, such as cyano. These unsaturated compounds include monoethylenically unsaturated compounds containing from 2 to 30 carbons such as ethylene, propylene, butene-1, pentene-2, hexene-2, etc., nonconjugated diethylenically unsaturated compounds such as allene, substituted compounds such as 3-pentenenitrile, 4-pentenenitrile, methyl pent-3-enoate, and ethylenically unsaturated compounds having perfluoroalkyl substituents such as, for example, $C_zF_{2z+1}$, where z is an integer of up to 20. The monoethylenically unsaturated compounds may also be conjugated to an ester group such as methyl pent-2-enoate.

The starting ethylenically unsaturated compounds useful in this invention and the hydrocyanation products thereof are those shown above in Formulas IX through XI. Those of Formula IX yield terminal nitriles of Formula X, while those of Formula XI yield terminal nitriles of Formula XII.

Preferred are nonconjugated linear alkenes, nonconjugated linear alkenenitriles, nonconjugated linear alkenoates, linear alk-2-enoates and perfluoroalkyl ethylenes. Most preferred substrates include 3- and 4-pentenenitrile, alkyl 2-, 3-, and 4-pentenoates, and $C_zF_{2z+1}CH{=}CH_2$ (where z is 1 to 12).

The preferred products are terminal alkanenitriles, linear dicyanoalkylenes, linear aliphatic cyanoesters, and 3-(perfluoroalkyl)propionitrile. Most preferred products are adiponitrile, alkyl 5-cyanovalerate, and $C_zF_{2z+1}CH_2CH_2CN$, where z is 1 to 12.

The present hydrocyanation process may be carried out, for example, by charging a reactor with the reactants, catalyst composition, and solvent, if any; but preferably, the hydrogen cyanide is added slowly to the mixture of the other components of the reaction. Hydrogen cyanide may be delivered as a liquid or as a vapor to the reaction. Another suitable technique is to charge the reactor with the catalyst and the solvent to be used, and feed both the unsaturated compound and the HCN slowly to the reaction mixture. The molar ratio of unsaturated compound to catalyst can be varied from about 10:1 to about 2000:1.

Preferably, the reaction medium is agitated, for example, by stirring or shaking. The reaction product can be recovered by conventional techniques such as, for example, by distillation. The reaction may be run either batchwise or in a continuous manner.

The hydrocyanation reaction can be carried out with or without a solvent. The solvent, if used, should be liquid at the reaction temperature and pressure and inert towards the unsaturated compound and the catalyst. Suitable solvents include hydrocarbons, such as benzene or xylene, and nitriles, such as acetonitrile or benzonitrile. In some cases, the unsaturated compound to be hydrocyanated may itself serve as the solvent.

The exact temperature is dependent to a certain extent on the particular catalyst being used, the particular unsaturated compound being used and the desired rate. Normally, temperatures of from −25° C. to 200° C. can be used, the range of 0° C. to 150° C. being preferred.

Atmospheric pressure is satisfactory for carrying out the present invention and hence pressures of from about 0.05 to 10 atmospheres (50.6 to 1013 kPa) are preferred. Higher pressures, up to 10,000 kPa or more, can be used, if desired, but any benefit that may be obtained thereby would probably not justify the increased cost of such operations.

HCN can be introduced to the reaction as a vapor or liquid. As an alternative, a cyanohydrin can be used as the source of HCN. See, for example, U.S. Pat. No. 3,655,723.

The process of this invention is carried out in the presence of one or more Lewis acid promoters which affect both the activity and the selectivity of the catalyst system. The promoter may be an inorganic or organometallic compound in which the cation is selected from scandium, titanium, vanadium, chromium, manganese, iron, cobalt, copper, zinc, boron, aluminum, yttrium, zirconium, niobium, molybdenum, cadmium, rhenium and tin. Examples include $ZnBr_2$, $ZnI_2$, $ZnCl_2$, $ZnSO_4$, $CuCl_2$, $CuCl$, $Cu(O_3SCF_3)_2$, $CoCl_2$, $CoI_2$, $FeI_2$, $FeCl_3$, $FeCl_2$, $FeCl_2(THF)_2$, $TiCl_4(THF)_2$, $TiCl_4$, $TiCl_3$, $ClTi(OiPr)_3$, $MnCl_2$, $ScCl_3$, $AlCl_3$, $(C_8H_{17})AlCl_2$, $(C_8H_{17})_2AlCl$; $(iso\text{-}C_4H_9)_2AlCl$, $Ph_2AlCl$, $PhAlCl_2$, $ReCl_5$, $ZrCl_4$, $NbCl_5$, $VCl_3$, $CrCl_2$, $MoCl_5$, $YCl_3$, $CdCl_2$, $LaCl_3$, $Er(O_3SCF_3)_3$, $Yb(O_2CCF_3)_3$, $SmCl_3$, $B(C_6H_5)_3$, $TaCl_5$. Suitable promoters are further described in U.S. Pat. Nos. 3,496,217; 3,496,218; and 4,774,353. These include metal salts (such as $ZnCl_2$, $CoI_2$, and $SnCl_2$), and organometallic compounds (such as $RAlCl_2$, $R_3SnO_3SCF_3$, and $R_3B$, where R is an alkyl or aryl group). U.S. Pat. No. 4,874,884 describes how synergistic combinations of promoters can be chosen to increase the catalytic activity of the catalyst system. Preferred promoters include $CdCl_2$, $FeCl_2$, $ZnCl_2$, $B(C_6H_5)_3$, and $(C_6H_5)_3SnX$, where $X=CF_3SO_3$, $CH_3C_6H_5SO_3$, or $(C_6H_5)_3BCN$. The mole ratio of promoter to nickel present in the reaction can be within the range of about 1:16 to about 50:1.

EXAMPLES

The following non-limiting, representative examples illustrate the process and catalyst compositions of this invention. All parts, proportions, and percentages are by weight, unless otherwise indicated. In each example, the following procedure was used unless otherwise noted.

The mixtures were heated in a thermostatically-controlled oil bath. HCN was delivered to the flask as an $HCN/N_2$ gas mixture by bubbling dry nitrogen carrier gas through liquid HCN maintained in an ice bath at 0° C. This provided a vapor stream which was about 35% HCN (vol/vol). Samples were periodically analyzed by gas chromatography (GC). In the examples, ADN stands for adiponitrile, MGN stands for 2-methylglutaronitrile, and ESN stands for ethylsuccinonitrile. COD stands for 1,5-cyclooctadiene and THF stands for tetrahydrofuran.

EXAMPLE 1

Synthesis of the Ligand "A" with Formula VI where each $R^9$, $R^{5'}$, $R^1$ are Hydrogen

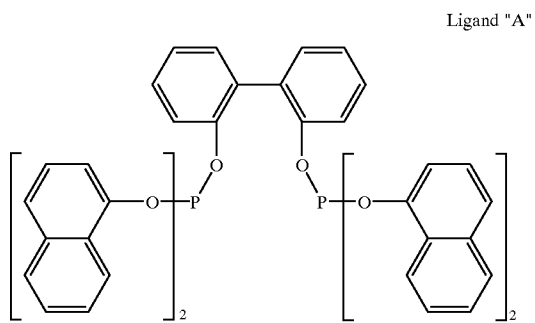

Ligand "A"

To a cooled solution (−30° C.) containing 1.154 g (8.0 mmol) of 1-naphthol and 0.55 g (2.4 mmol) of $PCl_3$ in 60 mL of toluene and 10 mL of THF was added slowly a cooled solution (−30° C.) containing 1.0 g (9.9 mmol) of $NEt_3$ in 20 mL of toluene. The mixture was warmed to room temperature and $^{31}P$ NMR of the reaction mixture in $C_6D_6$ showed one major peak at 162.5 ppm [the phosphorochloridite of 1-naphthol, $(1\text{-}C_{10}H_7O)_2PCl$] and the triarylphosphite $[(1\text{-}C_{10}H_7O)_3P]$ as minor peak at 130.1 ppm. A toluene solution containing 0.37 g (2.0 mmol) of 2,2'-biphenol and 0.4 g (4.0 mmol) of $NEt_3$ was added. The mixture was stirred for 0.5 hr, filtered through celite, washed with toluene, and the solvent evaporated under vacuum. The residue was vacuum dried to give 1.717 g of a brown paste. $^{31}P$ NMR in $C_6D_6$: 130.3 ppm along with minor peaks due to impurities at 143.6, 131.1, 129.4 ppm.

EXAMPLE 1A

Hydrocyanation of 3-Pentenenitrile with Ligand "A"/Ni(COD)$_2$ with Zinc Chloride Promoter 368 mg of Ligand "A", 40 mg Ni(COD)$_2$, and 20 mg of ZnCl$_2$ were dissolved in 5 mL of 3-pentenenitrile. The mixture was treated with HCN at a nitrogen flow rate of 30 mL/min at 70° C. for one hour. GC analysis indicated 38.8% ADN, 6.8% MGN, and 2.7% ESN (selectivity to ADN: 80.2%).

EXAMPLE 2

Synthesis of the Ligand "B" with Formula VI where each $R^1$ is 2-Propenyl, each $R^{5'}$ Ortho to Oxygen is Methoxy, and each $R^9$ is Hydrogen

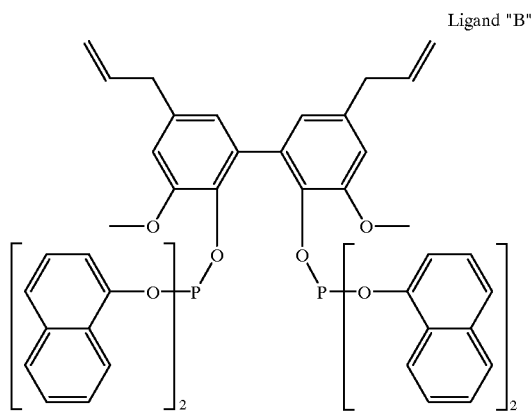

Ligand "B"

The same procedure as described in Example 1 was used to prepare the phosphorochloridite of 1-naphthol in situ except with 1.417 g (9.83 mmol) of 1-naphthol, 0.675 g (4.915 mmol) of PCl$_3$ and 1.1 g (11 mmol) of NEt$_3$. To this mixture was added 0.802 g (2.46 mmol) of 3,3'-dimethoxy-5,5'-di-2-propenyl-2,2'-dihydroxy-1,1'-biphenylene [prepared according to Dias, A., *Phytochemistry* 1988, 27, 3008] and 0.650 g (6.4 mmol) of NEt$_3$ in 15 mL of toluene. The mixture was stirred for two days at room temperature and worked up as described in Example 1 to give 2.475 g of a brown paste. $^{31}P$ NMR in $C_6D_6$: major peak at 133.7 ppm with minor peaks at 145.2, 137.3, 134.3, 131.1 ppm.

EXAMPLE 2A

Hydrocyanation of 3-Pentenenitrile with Ligand "B"/Ni(COD)$_2$ with Zinc Chloride Promoter 404 mg of Ligand "B" and 40 mg Ni(COD)$_2$ were dissolved in 5 mL of THF. The solvent was evaporated then 5 mL of 3-pentenenitrile and 20 mg of ZnCl$_2$ were added. The mixture was treated with HCN at a nitrogen flow rate of 30 mL/min at 70° C. for one hour. GC analysis indicated 62.3% ADN, 6.1% MGN, and 2.7% ESN (selectivity to ADN: 87.6%).

EXAMPLE 3

Synthesis of the Ligand "C" with Formula VI where each $R^5$ Ortho to Oxygen is Methoxy, each $R^9$ is Methoxy, and each $R^1$ is Methyl

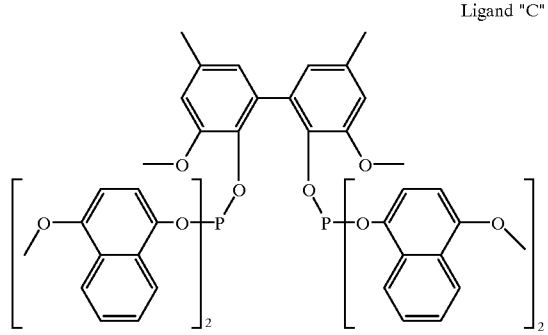

Ligand "C"

To a cooled solution (−30° C.) containing 1.395 g (8 mmoles) of 4-methoxy-1-naphthol and 0.55 g (4 mmoles) of PCl$_3$ in 80 mL of toluene and 5 mL of THF was added slowly a cooled solution (−30° C.) containing 0.875 g (8.7 mmoles) of NEt$_3$ in 20 mL of toluene. The mixture was warmed to room temperature. After stirring for about 45 minutes, the mixture was placed in a −30° C. freezer for 10 minutes. To this mixture was added 0.600 g NEt$_3$ (6 mmoles) and 2,2'-dihydroxy-3,3'-dimethoxy-5,5'-dimethyl-1,1'-biphenylene (550 mg, 2 mmoles), prepared by coupling 2-methoxy-4-methylphenol using the procedure described in *Phytochemistry* 1988, 27, 3008, in 15 mL of toluene. The mixture was stirred overnight, filtered through celite, washed with toluene and solvent removed under vacuum. The residue was vacuum dried to give 2.27 g of a brown solid. $^{31}$P NMR in C$_6$D$_6$: 133.76 ppm along with minor peaks for impurities at 145.46, 134.13, 133.56, 132.66, and 127.67 ppm.

EXAMPLE 3A

Hydrocyanation of 3-Pentenenitrile with Ligand "C"/Ni(COD)$_2$ with Zinc Chloride Promoter 404 mg of Ligand "C" and 40 mg Ni(COD)$_2$, were dissolved in 5 mL of THF. The solvent was evaporated then 5 mL of 3-pentenenitrile and 20 mg of ZnCl$_2$ were added. The mixture was treated with HCN at a nitrogen flow rate of 30 mL/min at 70° C. for one hour. GC analysis indicated 80.1% ADN, 5.8% MGN, and 2.0% ESN (selectivity to ADN: 91.2%).

EXAMPLE 4

Synthesis of Ligand "D" with Formula V where each $R^9$ is Methoxy and each $R^{5'}$ is Methyl Carboxylate

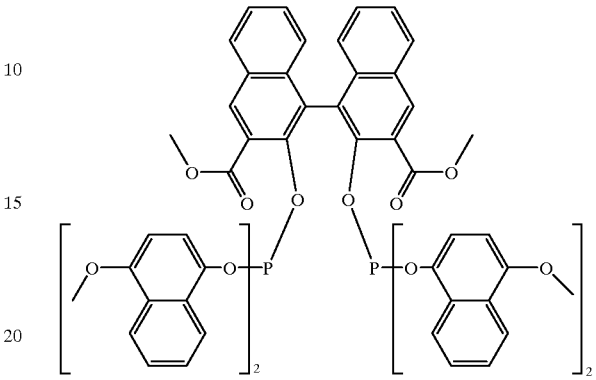

Ligand "D"

The synthesis utilized the same procedure described in Example 1 but substituting 1.394 g of 4-methoxy-1-naphthol for 1-naphthol and 0.809 g of dimethyl 2,2'-dihydroxy-1,1'-binaphthalene-3,3'-dicarboxylate, prepared according to the literature (*J. Am. Chem. Soc.* 1954, 76, 296 and *Tetrahedron Lett.* 1990, 413), for 2,2'-biphenol. $^{31}$P NMR (C$_6$D$_6$): major peak at 129.66 with minor peaks at 145.62, 132.65, 130.62 and 2.07 ppm due to impurities.

EXAMPLE 4A

Hydrocyanation of 3-Pentenenitrile with Ligand "D"/Ni(COD)$_2$ with Zinc Chloride Promoter 487 mg of Ligand "D", 40 mg Ni(COD)$_2$, and 20 mg of ZnCl$_2$ were dissolved in 5 mL of 3-pentenenitrile. The mixture was treated with HCN at a nitrogen flow rate of 30 mL/min at 70° C. for one hour. GC analysis indicated 28.7% ADN, 3.3% MGN, and 0.7% ESN (selectivity to ADN: 87.9%).

EXAMPLE 5

Synthesis of Ligand "E" with Formula V where each $R^9$ is Methoxy and each $R^{5'}$ is Hydrogen

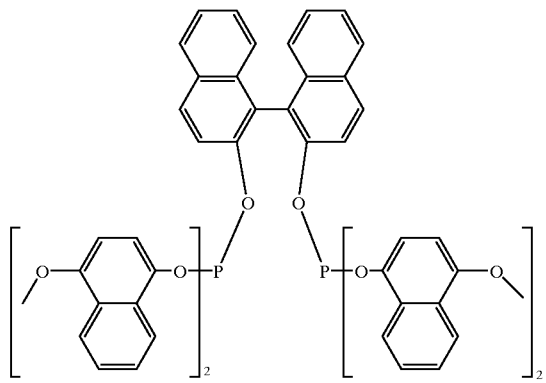

Ligand "E"

The synthesis utilized the same procedure described in Example 4 but substituted 0.573 g of 2,2'-binaphthol for dimethyl 2,2'-dihydroxy-1,1'-binaphthalene- 3,3'-dicarboxylate. $^{31}$P NMR (C$_6$D$_6$): 130.62 with minor peaks due to impurities at 144.61 and 132.80 ppm.

EXAMPLE 5A

Hydrocyanation of 3-Pentenenitrile with Ligand "E"/Ni(COD)$_2$ with Zinc Chloride Promoter 437 mg of Ligand "E" and 40 mg Ni(COD)$_2$ were dissolved in 5 mL THF. The solvent was evaporated then 5 mL of 3-pentenenitrile and 20 mg of ZnCl$_2$ were added. The mixture was treated with HCN at a nitrogen flow rate of 30 mL/min at 70° C. for one hour. GC analysis indicated 54.6% ADN, 10.3% MGN, and 4.4% ESN (selectivity to ADN: 78.8%).

EXAMPLE 6

Synthesis of Ligand "F" with Formula V where each R$^9$ is Hydrogen and each R$^{5'}$ is Hydrogen

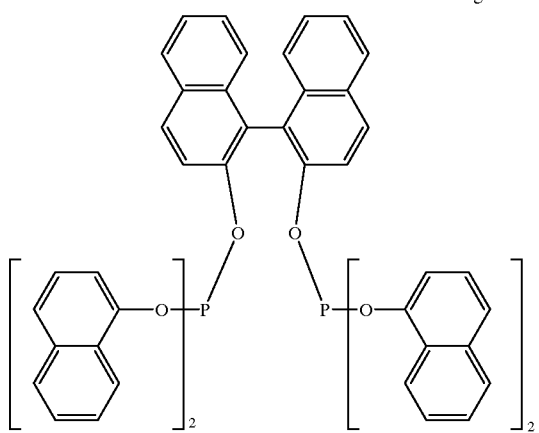

Ligand "F"

To a cooled solution (−30 to −40° C.) containing 8.650 g (60 mmoles) of 1-naphthol and 4.120 g (30 mmoles) of PCl$_3$ in 120 mL of toluene and 20 mL of THF was added slowly a solution containing 6.58 g (65 mmoles) of NEt$_3$ in 40 mL of toluene. The mixture was warmed to room temperature and stirred for 3 hours. A $^{31}$P NMR of the reaction mixture in C$_6$D$_6$ showed one major peak at 162.70 ppm and a minor peak at 130.96 ppm. A toluene solution containing 4.295 g (15 mmoles) of 2,2'-binaphthol and 3.5 g (35 mmoles) of NEt$_3$ was added. The mixture was stirred overnight, filtered through celite, washed with toluene, then the solvent was evaporated under vacuum. The residue was vacuum dried to give 9.228 g of an orange solid. $^{31}$P NMR in C$_6$D$_6$: 130.54 ppm along with minor peaks due to impurities at 144.49 and 131.14 ppm.

EXAMPLE 6A

Hydrocyanation of 3-Pentenenitrile with Ligand "F"/Ni(COD)$_2$ with Zinc Chloride Promoter 401 mg of Ligand "F", 40 mg Ni(COD)$_2$, and 20 mg of ZnCl$_2$ were dissolved in 5 mL of 3-pentenenitrile. The mixture was treated with HCN at a nitrogen flow rate of 30 mL/min at 70° C. for one hour. GC analysis indicated 38.5% ADN, 8.2% MGN, and 3.8% ESN (selectivity to ADN: 76.1%).

EXAMPLE 7

Synthesis of Ligand "G" with Formula VII where each R$^9$ is Hydrogen, each R$^{5'}$ Ortho to Oxygen is Methyl, each R$^1$ is Methyl, and X is CHCH$_3$

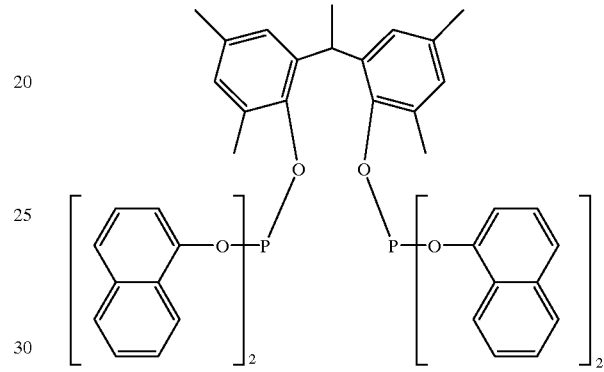

Ligand "G"

To 6.0 g (47 mmol) of 1-naphthol and 2.86 g (21 mmol) of PCl$_3$ in 40 mL of THF at −70° C. was added 5 g (50 mmol) of NEt$_3$ in 5 mL of THF. The mixture was stirred for 20 minutes then 2.81 g (10 mmol) of 2,2'-ethylidenebis(4,6-dimethylphenol) [prepared according to Yamada et. al., *Bull. Chem. Soc. Jpn.* 1989, 62, 3603] and 5 g (50 mmol) of NEt$_3$ in THF were added. The mixture was stirred overnight, filtered through Celite, then the solvent was removed by rotary evaporation. To the residue was added 100 mL of isopropyl alcohol. A solid formed which was collected and vacuum dried to give 7.7 g of the desired product as a light brown solid. $^{31}$P NMR (C$_6$D$_6$): 134.2 ppm. FABMS (m/z): Found: 903.38 (M$^+$+H); calculated for M$^+$+H (C$_{58}$H$_{48}$O$_6$P$_2$+H): 903.30.

EXAMPLE 7A

Hydrocyanation of 3-Pentenenitrile with Ligand "G"/Ni(COD)$_2$ with Zinc Chloride Promoter 380 mg of Ligand "G", 40 mg Ni(COD)$_2$, and 20 mg of ZnCl$_2$ were dissolved in 5 mL of 3-pentenenitrile. The mixture was treated with HCN at a nitrogen flow rate of 30 mL/min at 70° C. for one hour. GC analysis indicated 63.9% ADN, 13.9% MGN, and 2.8% ESN (selectivity to ADN: 89.5%).

EXAMPLE 8

Synthesis of Ligand "H" with Formula VI where each $R^9$ is Hydrogen, each $R^{5'}$ Ortho to Oxygen is Methoxy, and each $R^1$ is Methyl

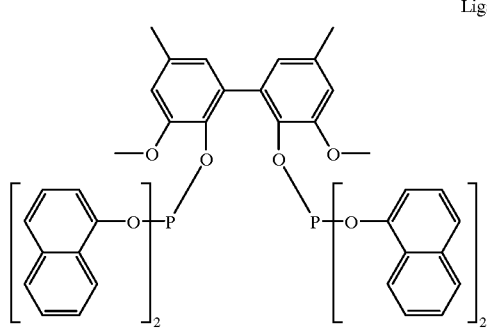

Ligand "H"

To 6.0 g (47 mmol) of 1-naphthol and 2.86 g (21 mmol) of $PCl_3$ in 40 mL of THF at −70° C. was added 5 g (49 mmol) of $NEt_3$ in 5 mL of THF. The mixture was stirred for 20 minutes then 2.85 g (10 mmol) of 3,3'-dimethoxy-5,5'-dimethyl-2,2'-dihydroxy-1,1'-biphenylene [prepared by coupling 2-methoxy-4-methylphenol using the procedure described in Phytochemistry 1988, 27, 3008] and 5 g (49 mmol) of $NEt_3$ in THF were added. The mixture was stirred overnight, filtered through Celite then the solvent was removed by rotary evaporation. The residue was treated with 100 mL of isopropyl alcohol. A solid formed which was collected and vacuum dried to give 7.45 g of the desired product as a light brown solid. $^{31}P$ NMR $(C_6D_6)$: 133.9 with minor peaks due to impurities at 145.1 and 131.0 ppm. FABMS (m/z): Found: 907.26 (M$^+$+H); calculated for M$^+$+H $(C_{56}H_{44}O_8P_2$+H$)$: 907.26.

EXAMPLE 8A

Hydrocyanation of 3-Pentenenitrile with Ligand "H"/Ni(COD)$_2$ with Zinc Chloride Promoter 381 mg of Ligand "H", 40 mg Ni(COD)$_2$, and 20 mg of ZnCl$_2$ were dissolved in 5 mL of 3-pentenenitrile. The mixture was treated with HCN at a nitrogen flow rate of 30 mL/min at 70° C. for one hour. GC analysis indicated 80.7% ADN, 6.9% MGN, and 2.6% ESN (selectivity to ADN: 89.5%).

EXAMPLE 9

Synthesis of Ligand "I" of Formula V where each $R^9$ is Hydrogen and each $R^{5'}$ is Isopropyl Carboxylate

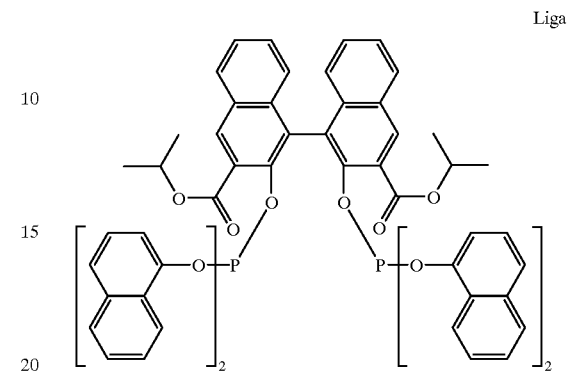

Ligand "I"

In the drybox, Et$_2$NPCl$_2$ (8.65 gm, 50 mmol) and 1-naphthol (14.4 gm, 100 mmol) were added to a 250 mL round bottom flask with a magnetic stirbar and 100 mL dry diethyl ether. Triethylamine (10.1 gm, 100 mmol) was added dropwise to the ether solution of PCl$_2$(NEt$_2$) and 1-naphthol at ambient temperature then the mixture was stirred overnight. A $^{31}P$ NMR analysis indicated that the reaction was complete (single signal at 140.5 ppm). The triethylammonium chloride salts were filtered from the ether solution then washed with dry ether (2×50 mL). The ether filtrates were evaporated to yield (1-C$_{10}$H$_9$O)$_2$PNEt$_2$ as an oil.

In the drybox, (1-C$_{10}$H$_9$O)$_2$PNEt$_2$ (3.89 gm, 10.0 mmol) was added to a 100 mL round bottom flask with a magnetic stirbar and 50 mL dry diethyl ether. A 1.0 M hydrogen chloride solution in ether (20.0 mL, 20.0 mmol) was added dropwise with a syringe. An analysis of the resulting ether solution by $^{31}P$ NMR indicated that (1-C$_{10}$H$_9$O)$_2$PNEt$_2$ had been completely converted to (1-C$_{10}$H$_9$O)$_2$PCl (δ=162.4 ppm). The diethylammonium chloride solids were separated from the ether solution by filtration then washed with dry ether (2×5 mL). The combined ether filtrates were cooled to −20° C. then diisopropyl 2,2'-dihydroxy-1,1'-binaphthalene-3,3'-dicarboxylate (2.29 gm, 5.0 mmol) was added followed by dry triethylamine (1.01 gm, 10.0 mmol) dropwise. The mixture was stirred at ambient temperature overnight. The triethylammonium salts were removed by filtration then the ether filtrate was evaporated. The residue was redissolved in dichloromethane then the product was precipitated with hexanes. This purification procedure was repeated three times to yield a white solid with a single $^{31}P$ NMR signal observed at 128 ppm in CDCl$_3$. FABMS (m/z): Found: 1092; calculated for M$^+$+H $(C_{68}H_{52}O_{10}P_2$+H$)$: 1092.

EXAMPLE 9A

Hydrocyanation of 3-Pentenenitrile with Ligand "I"/Ni(COD)$_2$ with Zinc Chloride Promoter 458 mg of Ligand "I" and 40 mg Ni(COD)$_2$ were dissolved in 5 mL of THF. The solvent was evaporated and 5 mL of 3-pentenenitrile and 20 mg of ZnCl$_2$ were added. The mixture was treated with HCN at a nitrogen flow rate of 30 mL/min at 70° C. for one hour. GC analysis indicated 69.3% ADN, 12.1% MGN, and 2.9% ESN (selectivity to ADN: 82.2%).

EXAMPLE 10

Synthesis of Ligand "J" of Formula V where each $R^9$ is Hydrogen and each $R^{5'}$ is Methoxy

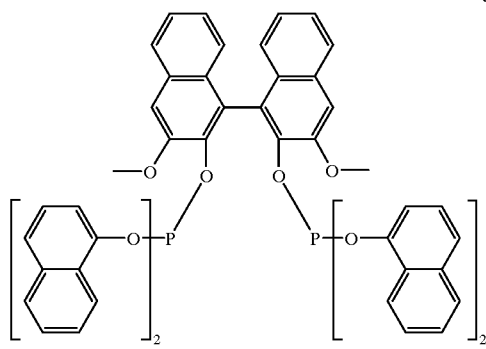

Ligand "J"

3,3'-Dimethoxy-2,2'-dihydroxy-1,1'-binaphthalene was prepared by oxidatively coupling 3-methoxy-2-naphthol (*Recl. Trav. Chim. Pays. Bas.* 1995, 112, 216) in toluene with oxygen and Cu(TMEDA)(OH)Cl catalyst as described in *Tetrahedron Lett.* 1990, 413. $^1$H NMR (CDCl$_3$, 300 MHz): 7.8 (d, 1H), 7.1–7.4 (m, 4H), 5.9 (bs, 1H), 4.1 (s, 3H) ppm. LCMS EI (m/z): Found: 346; calculated for M$^+$ (C$_{22}$H$_{18}$O$_4$): 346.

As described in Example 9, the phosphorochloridite of 1-naphthol, (1-C$_{10}$H$_9$O)$_2$PCl, was prepared by treating (1-C$_{10}$H$_9$O)$_2$PNEt$_2$ (5 mmol) in toluene (50 mL) with anhydrous 1.0 M HCl dissolved in ether (10 mmol). After separating the ammonium salts by filtration, the toluene/ether filtrate was cooled to −20° C. then 3,3'-dimethoxy-2, 2'-dihydroxy-1,1'-binaphthalene (0.692 gm, 2.0 mmol) was added followed by dry triethylamine (0.61 gm, 6 mmol) dropwise. The mixture was stirred at ambient temperature overnight. The triethylammonium salts were removed by filtration then the filtrate was evaporated to yield. $^{31}$P NMR (protio toluene): major signal at 131.6 ppm with minor signals at 131.2 and 145.8 ppm. FABMS (m/z): Found: 978; calculated for M$^+$+H (C$_{62}$H$_{44}$O$_8$P$_2$+H): 978.

EXAMPLE 10A

Hydrocyanation of 3-Pentenenitrile with Ligand "J"/Ni(COD)$_2$ with Zinc Chloride Promoter 411 mg of Ligand "J" and 40 mg Ni(COD)$_2$ were dissolved in 5 ML of THF. The solvent was evaporated and 5 mL of 3-pentenenitrile and 20 mg of ZnCl$_2$ were added. The mixture was treated with HCN at a nitrogen flow rate of 30 mL/min at 70° C. for one hour. GC analysis indicated 71.6% ADN, 6.5% MGN, and 2.8% ESN (selectivity to ADN: 88.5%).

EXAMPLE 11

Synthesis of Ligand "K" of Formula V where each $R^9$ is Hydrogen and one $R^{5'}$ is Phenyl Carboxylate and the other $R^{5'}$ is Hydrogen

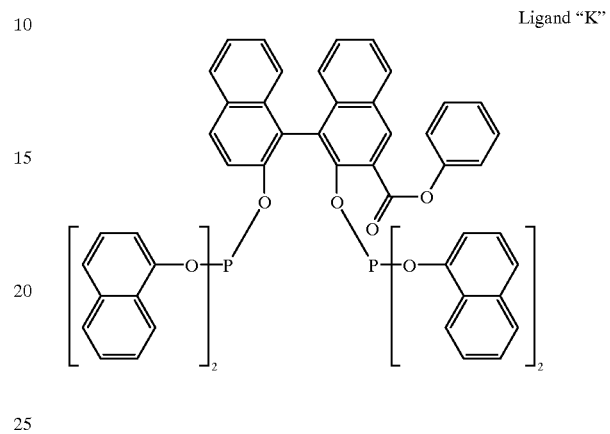

Ligand "K"

Phenyl 2,2'-dihydroxy-1,1'-binaphthalene-3-carboxylate was prepared by oxidative cross-coupling of phenyl 3-hydroxy-2-naphthoate with 2-naphthol (*Recl. Trav. Chim. Pays. Bas.* 1995, 112, 216) in toluene with oxygen and Cu(TMEDA)(OH)Cl catalyst as described in *Tetrahedron Lett.* 1990, 413. $^1$H NMR (CDCl$_3$, 300 MHz): 10.53 (s, 1H), 8.99 (s, 1H), 8.05–7.85 (m, 3H), 7.60–7.05 (m, 12H), 4.97 (s, 1H) ppm.

Using the procedure described in Example 9, Ligand "K" was prepared with the phosphorochloridite of 1-naphthol, [(1C$_{10}$H$_9$O)$_2$PCl] and phenyl 2,2'-dihydroxy-1,1'-binaphthalene-3-carboxylate. $^{31}$P NMR (protio toluene): major doublet signals at 130.4 and 129.4 ppm for Ligand "K" with minor impurity signals at 130.9, 145.0, and 146.2 ppm.

EXAMPLE 11A

Hydrocyanation of 3-Pentenenitrile with Ligand "K"/Ni(COD)$_2$ with Zinc Chloride Promoter 436 mg of Ligand "K" and 40 mg Ni(COD)$_2$ were dissolved in 5 mL of THF. The solvent was evaporated and 5 mL of 3-pentenenitrile and 20 mg of ZnCl$_2$ were added. The mixture was treated with HCN at a nitrogen flow rate of 30 mL/min at 70° C. for one hour. GC analysis indicated 60.8% ADN, 13.3% MGN, and 4.3% ESN (selectivity to ADN: 77.6%).

EXAMPLE 12

Synthesis of Ligand "L" of Formula V where each $R^9$ is Hydrogen and each $R^{5'}$ is Phenyl Carboxylate

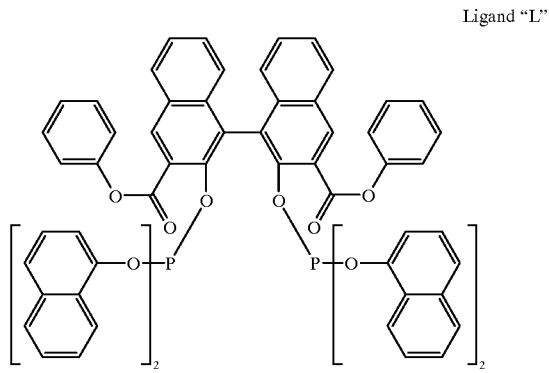

Ligand "L"

Diphenyl 2,2'-dihydroxy-1,1'-binaphthalene-3,3'-dicarboxylate was prepared by oxidative coupling of phenyl 3-hydroxy-2-naphthoate (*Recl. Trav. Chim. Pays. Bas.* 1995, 112, 216) in toluene with oxygen and CU(TMEDA)(OH)Cl catalyst as described in *Tetrahedron Lett.* 1990, 413. $^1$H NMR (CDCl$_3$, 300 MHz): 10.46 (s, 1H), 8.95 (s, 1H), 8.05–7.95 (m, 1H), 7.55–7.20 (m, 8H) ppm.

Using the procedure described in Example 9, Ligand "L" was prepared with the phosphorochloridite of 1-naphthol, [(1-C$_{10}$H$_9$O)$_2$PCl] and diphenyl 2,2'-dihydroxy-1,1'-binaphthalene-3,3'-dicarboxylate. $^{31}$P NMR (protio toluene): major signal at 128.6 ppm with minor signals at 129.6 and 130.8 ppm.

EXAMPLE 12A

Hydrocyanation of 3-Pentenenitrile with Ligand "L"/Ni(COD)$_2$ with Zinc Chloride Promoter 487 mg of Ligand "L" and 40 mg Ni(COD)$_2$ were dissolved in 5 mL of THF. The solvent was evaporated and 5 mL of 3-pentenenitrile and 20 mg of ZnCl$_2$ were added. The mixture was treated with HCN at a nitrogen flow rate of 30 mL/min at 70° C. for one hour. GC analysis indicated 22.7% ADN, 6.4% MGN, and 1.7% ESN (selectivity to ADN: 73.6%).

EXAMPLE 13

Synthesis of Ligand "M" of Formula V where each $R^9$ is Hydrogen and each $R^{5'}$ is Methyl

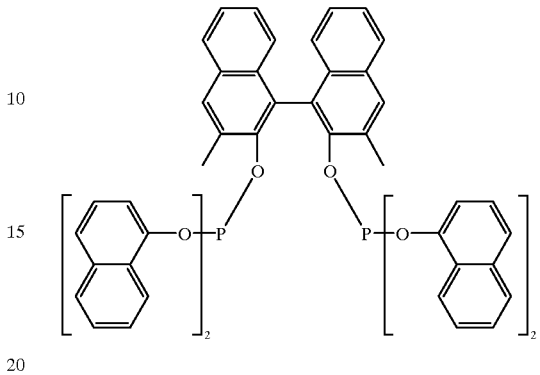

Ligand "M"

Using the procedure described in Example 9, Ligand "M" was prepared with the phosphorochloridite of 1-naphthol, [(1-C$_{10}$H$_9$O)$_2$PCl] and 3,3'-dimethyl-2,2'-dihydroxy-1,1'-binaphthalene. $^{31}$P NMR (protio toluene): major signal at 131.7 ppm with less intense signals at 130.7 and 142.6 ppm.

EXAMPLE 13A

Hydrocyanation of 3-Pentenenitrile with Ligand "M"/Ni(COD)$_2$ with Zinc Chloride Promoter 398 mg of Ligand "M" and 40 mg Ni(COD)$_2$ were dissolved in 5 mL of THF. The solvent was evaporated and 5 mL of 3-pentenenitrile and 20 mg of ZnCl$_2$ were added. The mixture was treated with HCN at a nitrogen flow rate of 30 mL/min at 70° C. for one hour. GC analysis indicated 46.0% ADN, 8.9% MGN, and 3.3% ESN (selectivity to ADN: 78.9%).

Comparative Example A

To 5 mL of THF was added 0.296 g (0.84 mmoles) of p-tritolylphosphite and 0.040 g (0.14 mmoles) of Ni(COD)$_2$. The THF was evaporated under vacuum. To the residue was added 5 mL of 3PN and 20 mg of ZnCl$_2$. The mixture was treated with HCN at a nitrogen flow rate of 30 mL/min at 70° C. for one hour. GC analysis indicated 37.5% ADN, 8.4% MGN and 1.3% ESN (selectivity to ADN: 79.4%).

Corporative Example B

To 5 ml of 3PN was added 0.099 g (0.28 mmoles) of p-tritolylphosphite and 0.205 g (0.14 mmoles) of tetrakis(p-tritolylphosphite)nickel. The mixture was treated with HCN at a nitrogen flow rate of 12 cc/min. After 1 hr of reaction, GC analysis indicated 26.5% ADN, 5.9% MGN and 0.8% ESN (selectivity to ADN: 79.8%). After 2 hr of reaction, GC analysis indicated 27.6% ADN, 6.1% MGN, 0.9% ESN (total conversion of PN to DN: 34.6%; selectivity to ADN: 79.8%).

Comparative Example C

Repeat of Comparative Example B: 24.6% ADN, 5.8% MGN, 0.9% ESN with 31.2% conversion of PN to DN and selectivity of 78.7% to ADN.

Comparative Example D 296 mg of p-tritolylphosphite and 40 mg of Ni(COD)$_2$ were dissolved in 5 mL of THF. The solvent was removed by vacuum evaporation. To the residue was added 5 ml of 3PN and 20 mg of ZnCl$_2$. The mixture was treated with HCN at a nitrogen flow rate of 12 mL/min at 70° C. for two hours. GC analysis indicated 22.7% ADN, 5.1% MGN, and 0.8% ESN (selectivity to ADN: 79.4%).

Comparative Example E

To 5 ml of 3PN was added 0.306 g (0.89 mmoles) of p-tritolyphosphite and 0.115 g (0.14 mmoles) of (oTTP)2Ni (ethylene) (oTTP=o-tritolyphosphite) and 0.020 g of ZnCl$_2$. The mixture was treated with HCN at a nitrogen flow rate of 30 ml/min at 70° C. for one hour. GC analysis indicated 28.6% ADN, 5.9% MGN and 0.9% ESN (selectivity to ADN: 80.7%; total conversion of PN to DN: 35.4%).

Although particular embodiments of the present invention have been described in the foregoing description, it will be understood by those skilled in the art that the invention is capable of numerous modifications, substitutions and rearrangements without departing from the spirit or essential attributes of the invention. Reference should be made to the appended claims, rather than to the foregoing specification, as indicating the scope of the invention.

We claim:

1. A hydrocyanation process comprising reacting an acyclic, aliphatic, monoethylenically unsaturated compound in which the ethylenic double bond is not conjugated to any other olefinic group in the molecule, with a source of HCN in the presence of a catalyst precursor composition comprising a Lewis acid, a zero-valent nickel, and at least one multidentate phosphite ligand selected from the group represented by the following Formulas I, II, III, IV, V, VI, VII and VIII:

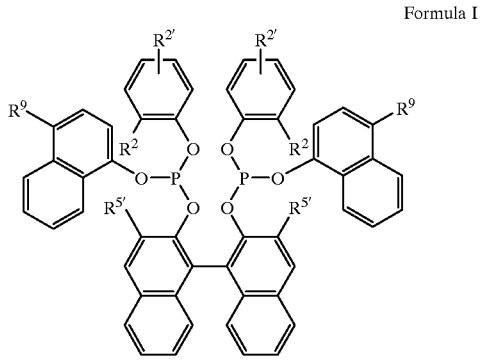

Formula I

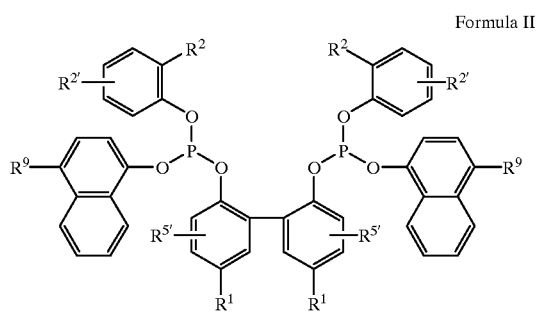

Formula II

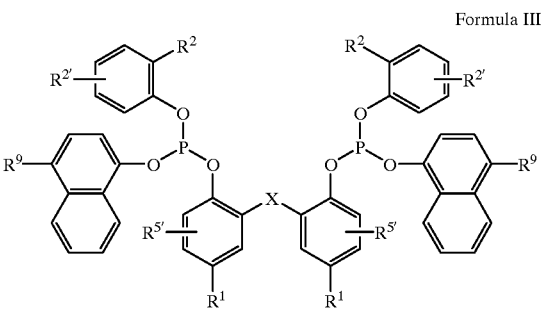

Formula III

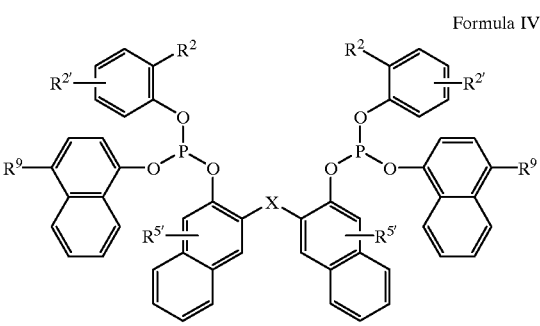

Formula IV

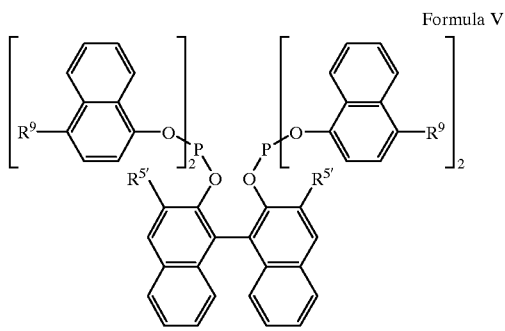

Formula V

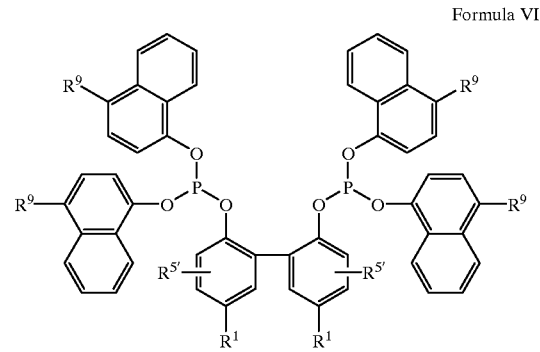

Formula VI

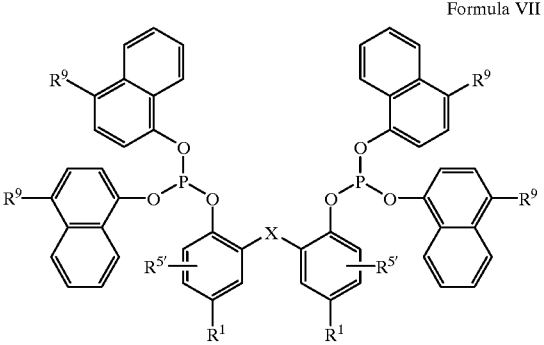

Formula VII

-continued

Formula VIII

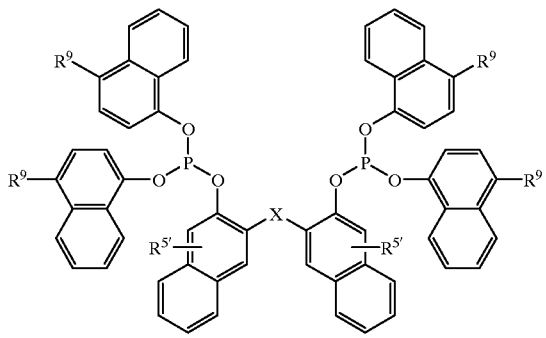

wherein
- each $R^1$ is independently a H, halogen, primary, secondary, or tertiary hydrocarbyl of 1 to 12 carbon atoms, $OR^3$ wherein $R^3$ is a $C_1$ to $C_{12}$ alkyl, or $CO_2R^{3'}$ wherein $R^{3'}$ is a $C_1$ to $C_{12}$ alkyl, or aryl;
- each $R^2$ and $R^{2'}$ are independently a H, halogen, primary, secondary or tertiary hydrocarbyl of 1 to 12 carbon atoms, $OR^3$ wherein $R^3$ is a $C_1$ to $C_{12}$ alkyl, or $CO_2R^{3'}$ wherein $R^{3'}$ is a $C_1$ to $C_{12}$ alkyl, or aryl; when $R^{2'}$ is not hydrogen, $R^{2'}$ cannot be ortho to the oxygen;
- each $R^{5'}$ is independently a H, halogen, primary, secondary or tertiary hydrocarbyl of 1 to 12 carbon atoms, $OR^3$ wherein $R^3$ is a $C_1$ to $C_{12}$ alkyl, or $CO_2R^{3'}$ wherein $R^{3'}$ is a $C_1$ to $C_{12}$ alkyl, or aryl;
- each $R^9$ is independently H, halogen, primary, secondary or tertiary hydrocarbyl of 1 to 12 carbon atoms, $OR^3$ wherein $R^3$ is a $C_1$ to $C_{12}$ alkyl, or $CO_2R^{3'}$ wherein $R^{3'}$ is a $C_1$ to $C_{12}$ alkyl, or aryl; and
- each X is independently O or $CH(R^{4'})$, wherein $R^{4'}$ is H, aryl, or a $C_1$ to $C_{12}$ alkyl.

2. The process of claim 1 wherein the starting ethylenically unsaturated compound is selected from the group consisting of the compounds of the following Formulas IX and XI:

$$CH_3—(CH_2)_y—CH=CH—(CH_2)_x—R^5 \quad (IX)$$

$$CH_2=CH—(CH_2)_x—R^5 \quad (XI),$$

wherein
- $R^5$ is H, CN, $CO_2R^{3'}$, or perfluoroalkyl;
- y is an integer of 0 to 12;
- x is an integer of 0 to 12 when $R^5$ is H, $CO_2R^{3'}$ or perfluoroalkyl;
- x is an integer of 1 to 12 when $R^5$ is CN; and
- $R^{3'}$ is a $C_1$ to $C_{12}$ alkyl, or aryl.

3. The process of claim 1 wherein the starting monoethylenically unsaturated compound is selected from the group consisting of 3-pentenenitrile, 4-pentenenitrile; alkyl 2-, 3-, and 4-pentenoates, and $C_zF_{2z+1}CH=CH_2$, where z is an integer of 1 to 12.

4. The process of claim 3 wherein the starting monoethylenically unsaturated compound is 3-pentenenitrile or 4-pentenenitrile.

5. The process of claim 1 which is carried out at a temperature of −25° C. to 200° C. and at a pressure of 50.6 to 1013 kPa.

6. The process of claim 5 which is carried out at atmospheric pressure and at a temperature of 0° C. to 150° C.

7. The process of claim 1 wherein the Lewis acid is selected from the group consisting of inorganic or organometallic compounds in which the cation is selected from scandium, titanium, vanadium, chromium, manganese, iron, cobalt, copper, zinc, boron, aluminum, yttrium, zirconium, niobium, molybdenum, cadmium, rhenium and tin.

8. The process of claim 7 wherein the Lewis acid is selected from the group consisting of $ZnBr_2$, $ZnI_2$, $ZnCl_2$, $ZnSO_4$, $CuCl_2$, $CuCl$, $Cu(O_3SCF_3)_2$, $CoCl_2$, $CoI_2$, $FeI_2$, $FeCl_3$, $FeCl_2(tetrahydrofuran)_2$, $TiCl_4(tetrahydrofuran)_2$, $FeCl_2$, $TiCl_4$, $TiCl_3$, $ClTi(OiPr)_3$, $MnCl_2$, $ScCl_3$, $AlCl_3$, $(C_8H_{17})AlCl_2$, $(C_8H_{17})_2AlCl$, $(iso-C_4H_9)_2AlCl$, $(phenyl)_2AlCl$, $phenylAlCl_2$, $ReCl_5$, $ZrCl_4$, $NbCl_5$, $VCl_3$, $CrCl_2$, $MoCl_5$, $YCl_3$, $CdCl_2$, $LaCl_3$, $Er(O_3SCF_3)_3$, $Yb(O_2CCF_3)_3$, $SmCl_3$, $TaCl_5$, $CdCl_2$, $B(C_6H_5)_3$, and $(C_6H_5)_3SnX$, where $X=CF_3SO_3$, $CH_3C_6H_5SO_3$, or $(C_6H_5)_3BCN$.

* * * * *